United States Patent [19]

Ferree et al.

[11] Patent Number: 4,699,008
[45] Date of Patent: Oct. 13, 1987

[54] APPARATUS FOR ULTRASONICALLY INSPECTING A LARGE SHAFT FROM A LIQUID-FILLED BORE

[75] Inventors: Herbert E. Ferree, Hempfield Township, Westmoreland County, Pa.; Lawrence D. Nottingham, Orlando, Fla.

[73] Assignee: Westinghouse Electric Corp., Pittsburgh, Pa.

[21] Appl. No.: 844,499

[22] Filed: Mar. 26, 1986

[51] Int. Cl.[4] .......................................... G01N 29/04
[52] U.S. Cl. ................................................. 73/623
[58] Field of Search .................................. 73/623, 644

[56] References Cited

U.S. PATENT DOCUMENTS

| | | | |
|---|---|---|---|
| 4,058,000 | 11/1977 | Ries et al. | 73/644 |
| 4,307,612 | 12/1981 | Elsley et al. | 73/623 |
| 4,361,044 | 11/1982 | Kupperman et al. | 73/623 |
| 4,523,470 | 6/1985 | Müller et al. | 73/623 |

Primary Examiner—Anthony V. Ciarlante
Attorney, Agent, or Firm—F. J. Baehr, Jr.

[57] ABSTRACT

A shipping and storage enclosure for an ultrasonic inspection system used to inspect turbine and generator rotors from the bore which is flooded with water and which enclosure can be expanded into an operating enclosure in which the environment is controlled to provide for affective operation of the equipment and provide for alignment of the ultrasonic sensing head with the bore of the rotor shaft.

20 Claims, 7 Drawing Figures

APPARATUS FOR ULTRASONICALLY INSPECTING A LARGE SHAFT FROM A LIQUID-FILLED BORE

BACKGROUND OF THE INVENTION

This invention relates to ultrasonic inspection of steel shafts and more particularly to ultrasonicly inspecting large diameter shafts from bores filled with a liquid.

When ultrasonics are utilized to inspect a large mass of metal, a liquid film is used as a medium to transmit ultrasonic sound from the transducer into the metal, however, when only a thin film separates the transducer or sonic lens from the metal, near surface flaws are often not distinguishable. By moving the transducers a greater distance from the surface, indications of sonic reflections near the surface may become more distinguishable. Since in shafts rotating at high speeds the area adjacent the bore is highly stressed and imperfections in this area will affect the life of the shaft, an inspection system should have good resolution near the bore and this may be accomplished by moving the transducer away from the bore surface improving the near bore resolution of sonic reflectors.

Large shafts such as in turbine and generator rotors are expensive to manufacture and because of their expense spare rotors are usually not available. The inspection of such rotors require a large amount of machinery down-time and if the rotors must be shipped to a special inspection location down-time is even greater. A system developed by Southwest Research Institute in joint sponsorship with the Electric Power Research Institute called Turbine Rotor Examination Evaluation System, TREES, uses twelve focus search transducers to determine flaw size. The transducers are utilized in a liquid-filled bore. Though the literature says the unit is enclosed in a portable container for easy transportation to field sites, the container is not expandable to provide an enclosed work station at the side of the inspection.

SUMMARY OF THE INVENTION

In general, apparatus for ultrasonicly inspecting a large shaft from a bore filled with liquid comprises a head assembly having at least one transducer disposed thereon to provide indications of defects within the shaft and means for supporting the head assembly concentrically in the bore, a plurality of tubular extensions which fasten to each other and to the head, a cable electrically connected to the head assembly and threaded through the tubular extensions. The apparatus also has a trough which is partially filled with liquid during the ultrasonic inspection and has mounted on each end thereof means for raising and lowering the trough, a round tube generally the same diameter as the bore is mounted in the trough and is axially aligned with the bore. The apparatus also comprises a drive for moving the tubular exensions and head assembly axially and rotatably and means for producing a signal indicative of the axial and rotational position of the head assembly together with means for producing, receiving and processing ultrasonic and positional signals to operate the apparatus and to produce intelligible information about the location and size of ultrasonic flaw indications in the shaft. The apparatus also comprises an enclosure having floor, wall and roof portions for storing, shipping and operating the elements of the apparatus described herein and controlling the environment within the enclosure so that it is suitable for the apparatus and those who operate it.

BRIEF DESCRIPTION OF THE DRAWINGS

The objects and advantages of this invention will become more apparent by reading the following detailed description in conjunction with the accompanying drawings, in which.

DESCRIPTION OF THE PREFERRED EMBODIMENT

Figure 1:
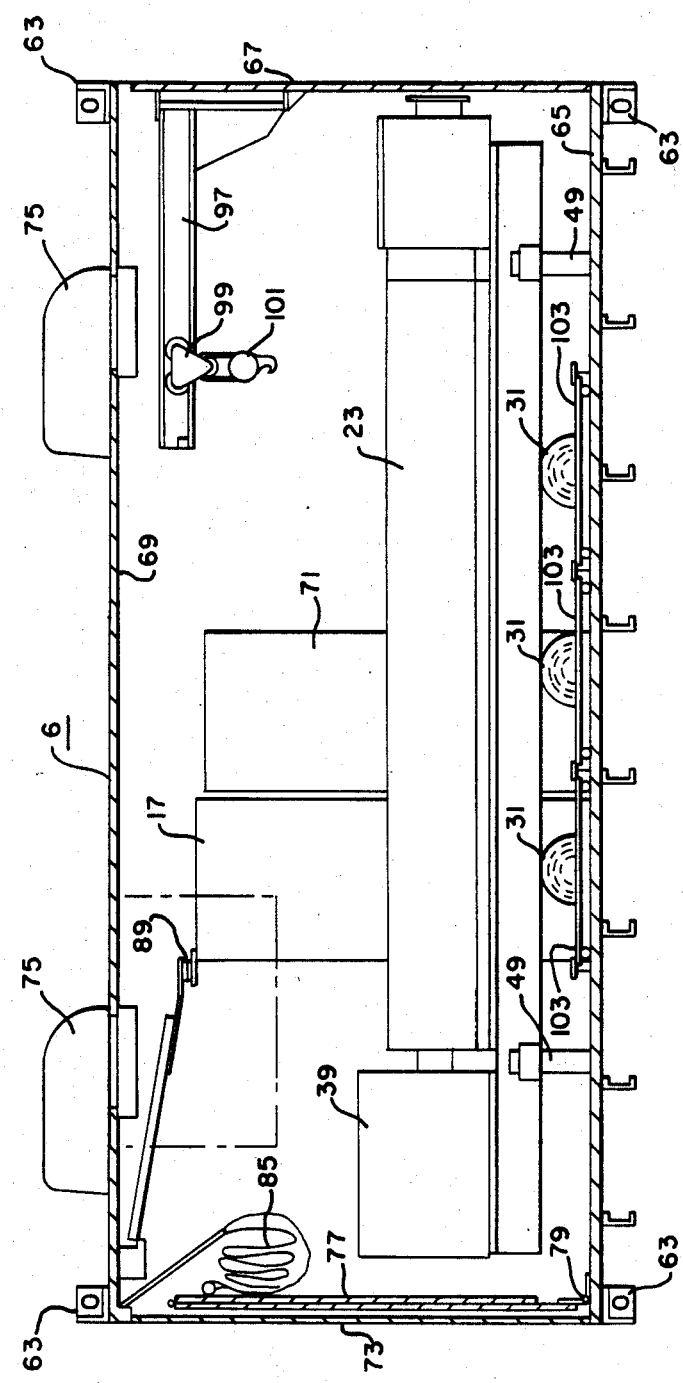
FIG. 1 is a sectional view of a shipping, storage and operating enclosure for an ultrasonic inspection apparatus operable in a liquid-filled bore of a large shaft.

Referring now to the drawings in detail, there is shown apparatus 1 for ultrasonicly inspecting a large shaft 3 from a liquid-filled bore 5.

Figure 7:
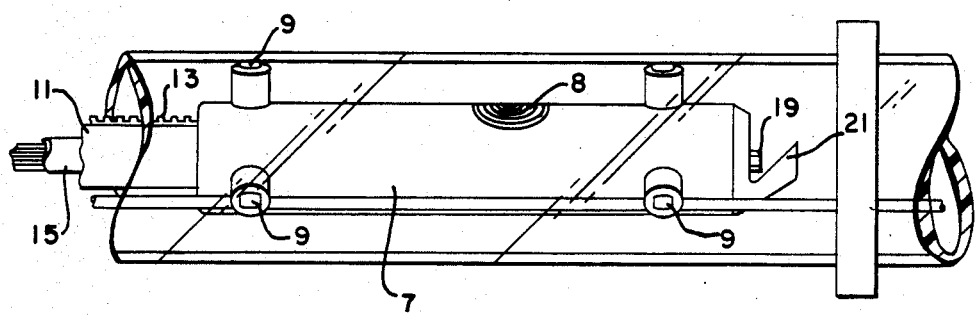
FIG. 7 is an elevational view of an ultrasonic head disposed in a transparent tube which fits in the trough.

The apparatus, as shown in FIG. 1, comprises an expandable, shipping and storage container, an enclosure 6 which, when expanded, provides an enclosed controlled environment for operating the ultrasonic inspection equipment which, as shown in FIG. 7, comprises an ultrasonic head 7 having at least one dynamically focused ultrasonic transducer 8 disposed thereon and a plurality of roller feet 9, which are driven outwardly by a motor or other means (not shown) to engage the bore surface and generally support the ultrasonic head 7 so that it is centrally disposed in the bore 5. A plurality of square tubular bars 11 fasten together to move the ultrasonic head 7 in the bore 5. The bars 11 have a gear rack 13 disposed on one side for advancing and retracting the ultrasonic head 7. The square shaped tube is also adapted to slide through the rotatable square hole for turning the ultrasonic head 7 in the bore 5. The opening in the tubular bar 11 provides a cable and tubing run for a cable 15 and tubing (not shown) utilized to connect the ultrasonic head 7 to a computer 17 and to remove air from the bore, respectively.

Besides the dynamically focused ultrasonic transducer 8 for detecting sonic reflectors in the shaft, there is also another transducer 19 which reflects a signal off an inclined surface 21 to determine the position of the ultrasonic head 7 with respect to the axis of the bore 5.

To operate the ultrasonic system 1, the computer 17 or other device produces input signals for the transducers 8 and 19 and processes reflected signals received by the transducers 8 and 19. The computer 17 also produces signals to position the ultrasonic head 7 in the bore 5 and processes signals indicative of the position of the ultrasonic head and the transducer 8 as it progress through the bore 5.

Figure 2:
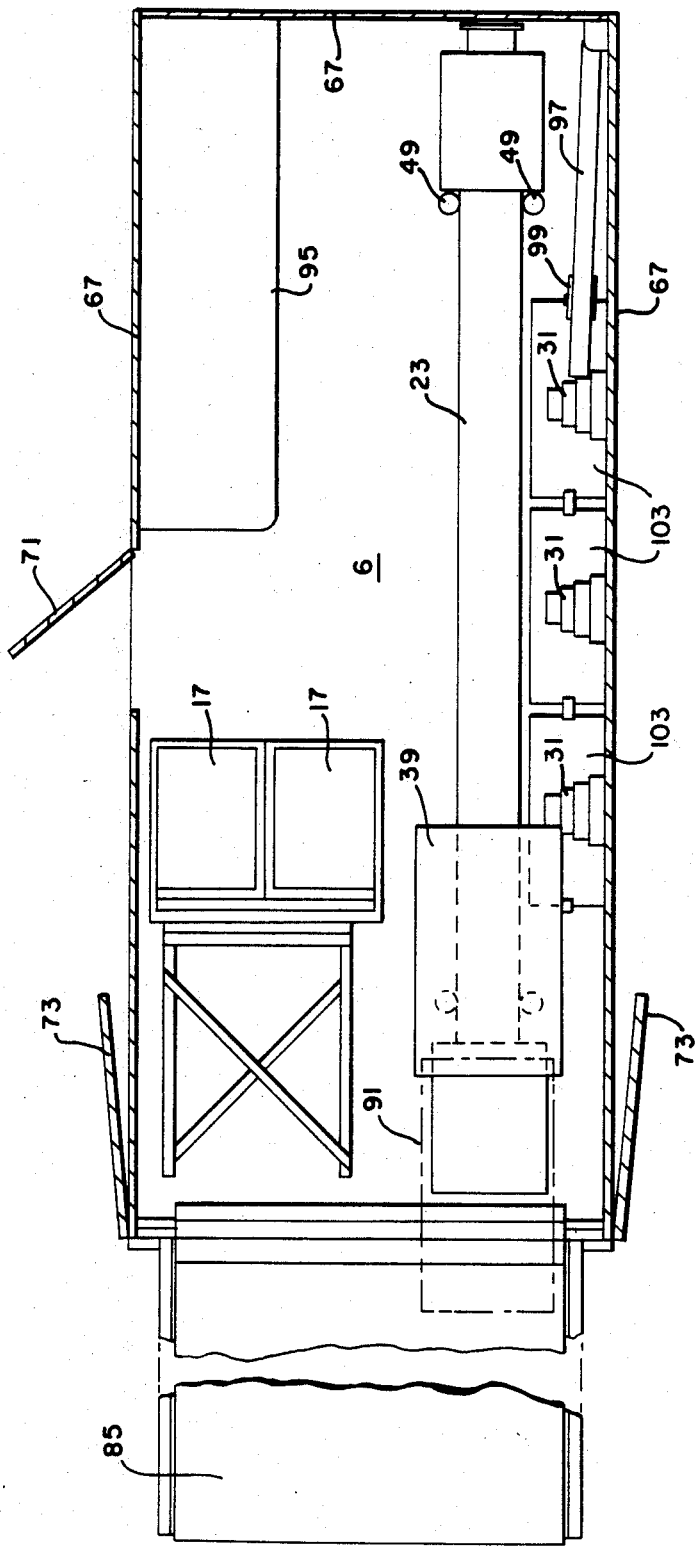
FIG. 2 is a plan view of an expandable operating enclosure extending from the storage and shipping enclosure.
Figure 3:
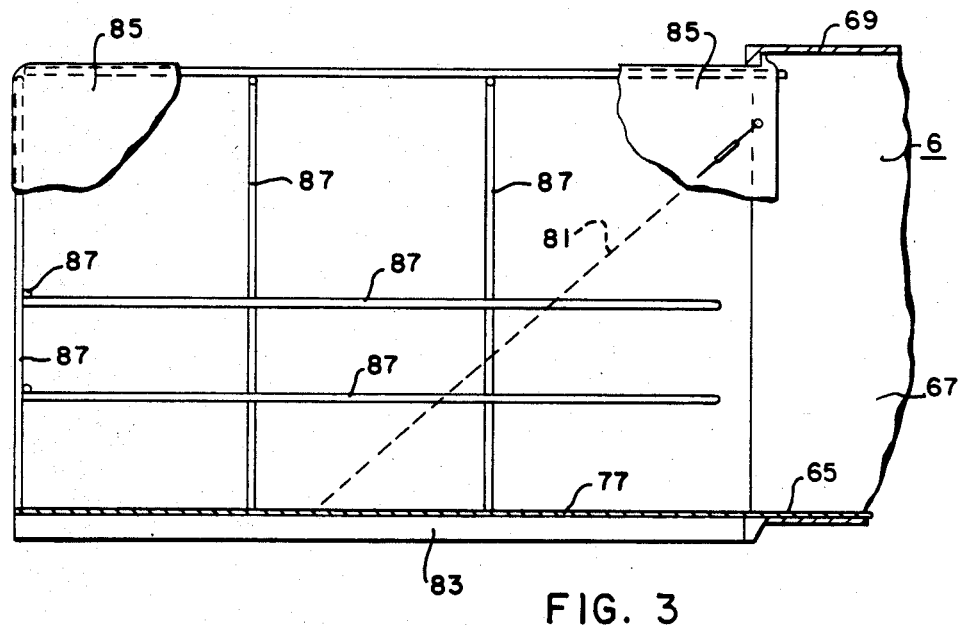
FIG. 3 is a detailed sectional view of the expanded operating area.
Figure 4:
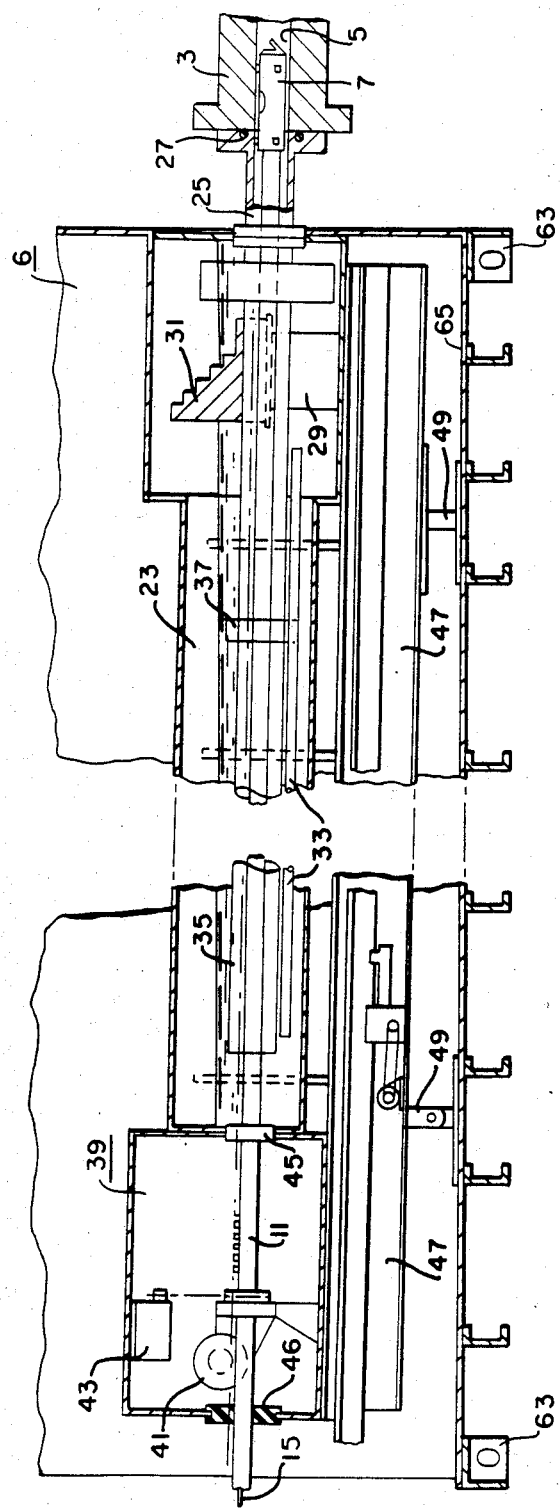
FIG. 4 is an elevational view of a liquid trough which is connected to the bore.
Figure 6:
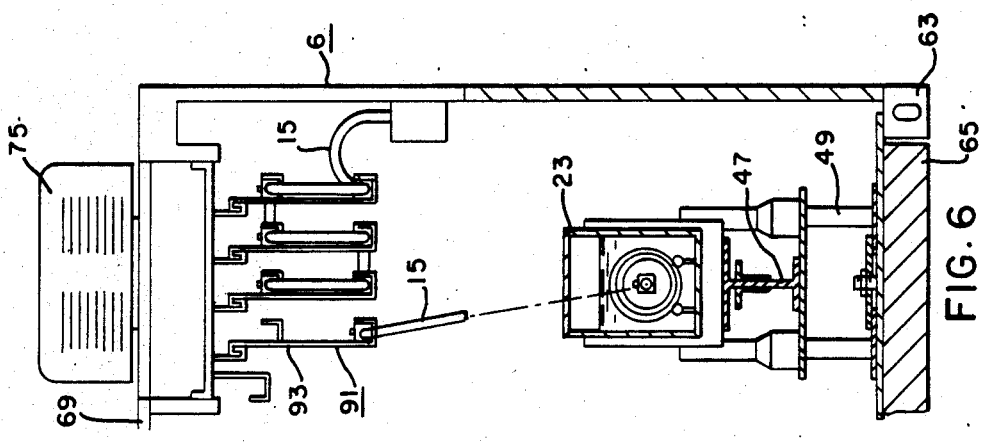
FIG. 6 is a sectional view taken on line VI—VI of FIG. 5.

Since the bore 5 is flooded with liquid during inspection, an elongated trough 23, as shown in FIGS. 2, 4 and 6, is partially filled with liquid and is connected to one end of the shaft 3 by a transparent spool piece 25 which has O-ring seals 27 or other sealing means disposed on each end thereof. The shaft 3 and bore 5 along with the trough 23 are inclined so that gas bubbles formed in the bore 5 will come to the surface of the liquid in the trough 23.

The trough 23 also provides access to the ultrasonic head 7 and transducers 8 and 19 while they are submerged outside of the bore 5. A calibration block mount 29 is disposed in the end of the trough 23 which is connected to the shaft 3 to receive semicircular calibration blocks 31. A pair of rails 33 are disposed in the trough 23 so as to support a transparent pipe 35 axially aligned with the bore 5 of the shaft 3. When inspecting steam turbine and generator rotor shafts, the largest bores encountered are about 7 to 7½ inches in diameter so that the rail is disposed to position an 8-inch outside diameter transparent pipe so it is axially aligned with the bore 5. If the bore 5 is smaller in diameter, transparent pipes 35 generally the same inside diameter as the bore 5, are utilized and have collars 37 with an outside diameter of 8 inches spaced at intervals to align the axis of the smaller diameter transparent pipes 35 with the axis of the bore 5.

Mounted on the end of the trough 23 opposite the shaft 5 is a drive 39, which cooperates with the tubular bars 11 to move the ultrasonic head 7 in axial and rotational directions in response to signals from the computer 17 and produces signals indicative of the axial and rotational position of the ultrasonic head 7 and transducer 8, which signals are returned to the computer 17.

The drive 39 comprises an axial drive and signal portion 41 and a rotational drive and signal portion 43. The tubular bars 11 pass through the drive 39 and there are liquid seals 45 disposed adjacent the trough 23 and a rotatable support 46 is provided on the other end of the drive 39.

The trough 23 and drive 39 for the tubular bars 11 are mounted on an I-beam 47 which provides a rigid base to maintain alignment of the guide rails 33, drive 39 and calibration block mount 29 once proper alignment has been achieved. The I-beam 47 is mounted on adjustable legs 49 which allow the trough to be inclined to align it with the inclined shaft 3. Besides moving up and down on both ends the legs 49 can also be moved side ways to align the trough with the shaft. One set of legs 49 also slides back and forth as the inclination of the trough 23 is altered to conform with shaft alignment. Alignment should be within ±0.10 inches and may be performed utlizing a builders level, tight wire method or a laser alignment system.

A track 51 extends from the end of the I-beam 47 opposite the shaft 3 and has a carriage 53 which runs thereon. A support 55 with an opening for receiving the tubular bar 11 is disposed on one end of the carriage 53 and an elongated support 57 is disposed on the other end of the carriage 53 for receiving the tubular bar 11 or the cable 14 to support the portion of the tubular bar 11 and cabe 15 extending beyond the drive 39. The computer 17, trough 23, the ultrasonic head 7 and all the support equipment associated with the operation is mounted, installed, stored, transported in and operated from the enclosure 6 which can be transported by truck, aircraft or sea-going vessel with adequate provisions for protecting the sensitive equipment.

The enclosure 6 has an outside dimension approximately 8'×8½'×20' and is built like an enclosed truck body without wheels except that all eight corners have standard lifting or tie-down lugs 63 attached to a reinforced frame structure within the enclosure 6.

The enclosure 6 has a floor 65, wall 67 and a roof and ceiling 69. There are two doors, an entrance door 71 and a double door 73, which opens one end of the enclosure 6. Mouted on and extending through the roof and ceiling 69 are two air-conditioning units 75 to control the temperature in the enclosure 6 for the efficient operation of the equipment and the people operating it. The enclosure 6 is provided with a transformer with variable taps so that a single high-voltage line can be hooked up to the transformer and the voltage reduced to various levels to provide the proper power for the air-conditioner 75, computer 17, motors, lighting and other electrical requirements.

Behind the double doors 73 on one end of the enclosure 6 is an expandable portion which comprises a floor portion 77 which folds up into the end of the enclosure 6 is hinged at the floor 65 and has a hinge 79 disposed in the middle which generally rotates 180° so that the floor portions 77 also folds on itself, thus providing a floor extension which is generally twice as long as the walls 67 are high. A pair of cables 81 are connected between the upper portion of the walls 67 and the outer portion of a frame support 83, which helps support the extended floor portion 77. The frame support 83 fits under the extended floor portion 77 and attaches to the enclosure 6 to provide further support for the extended floor portion 77. The frame support 83 is formed from aluminum channels and can be disassembled and stored in the enclosure 6 when the equipment is prepared for storage and shipment.

A fabric tent-like portion 85 extends from and is connected from the ceiling 69 and wall 67 and tubular supports 87 connect to the floor extension 77 to form a frame over which the fabric tent-like portion 85 is stretched substantially increasing the enclosed area and providing additional work area within a controlled environment from which to operate the apparatus.

The computer 17 is mounted in the enclosure 6 with shock-absorbing mounts 89 to protect it during storage and when in transit.

Figure 5:
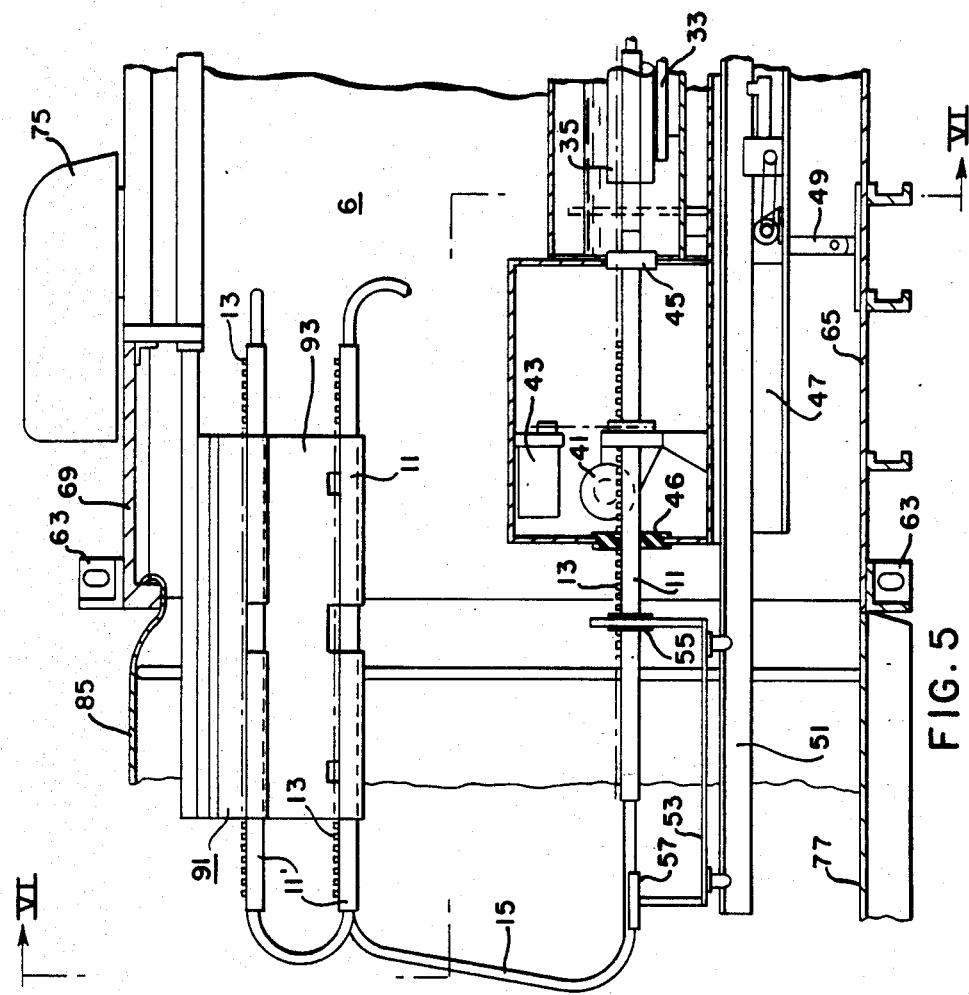
FIG. 5 is a sectional view of the apparatus utilized to position an ultrasonic head in the liquid-filled bore.

The cable 15 is continuous and connects the ultrasonic head 7 and transducers 8 and 19 to the computer 17 and is threaded serially through the tubular bars 11. When the apparatus is being operated, when it is in storage or during shipment, the tubular bars with the cable 15 extending therethrough are stored in a rack 91. As shown in FIGS. 5 and 6, the rack 91 comprises a plurality of sheet metal carriages 93 which provide means for holding one or more tubular bars 11 and are removably fastened to a slidable base portion 94 which allows the tubular bars 11 to be stored in the enclosure 6 above the trough 23 and slide out into the expanded enclosure during operation of the ultrasonic equipment.

The carriage 93 can be removed from the rack 91 with the tubular bars 11 and cable 15 in place thereon and the carriage 93 is hooked on brackets on the tubular supports 87 for the tent-like structure 85 improving the positioning before the tubular bars 11 are serially attached to the utrasonic head 7.

Work stations 94 for operating the computer 17 are disposed in the enclosure 6 opposite the trough 23.

An I-beam 97 is pivotally mounted in the corner of the enclosure 61 adjacent the end of the trough 23 which has the calibration block mount 29. A trolley 99 rolls on the I-beam 97 and has a hoist 101 attached thereto to install and remove the calibration blocks 31 from the trough 23. The calibration blocks 31 are stored on dollies 103 to which they are fastened during storage and shipment. The dollies 103 have bolts or other means for fastening them to the floor 69 so that they will not move during storage or shipment but provide easy access during the operation of the equipment even though the calibration blocks weigh hundreds of pounds.

In the enclosure is also a water treatment system 105 which filters and deaerates the water or liquid utilized to fill the shaft and trough.

The apparatus hereinbefore described provides a shipping and storage enclosure for an ultrasonic inspection system wherein the shipping and storage enclosure is easily expanded into an operating enclosure in which the environment is controlled for the effective operation of the equipment and the people necessary to operate the equipment.

What is claimed is:

1. Apparatus for ultrasonicly inspecting a large shaft from a bore filled with liquid, comprising:
    a head assembly having at least one transducer disposed thereon for indicating sonic reflectors within the shaft and means for supporting said head concentrically in said bore;
    a plurality of tubular extensions which fasaten to each other and to said head assembly;
    a cable electrically connected to said transducer and said head assembly and threaded through said tubular extensions;
    a trough which is partially filled with liquid during the ultrasonic inspection and having mounted on each end thereof means for raising and lowering the trough;
    a round tube generally the same diameter as said bore mounted in said trough and axially aligned with said bore during the ultrasonic inspection;
    drive means for moving said tubular extensions and head assembly axially and rotationally;
    means for producing a signal indicative of the axial and rotational position of said head assembly and transducer;
    means for providing, receiving and processing ultrasonic and positional signals to operate the apparatus and to produce intelligible information about the location and size of sonic reflectors in said shaft;
    an enclosure having floor, wall and roof portions for storing, shipping and operating said elements of said apparatus described herein and controlling the environment within said enclosure so that the environment is suitable for said apparatus and those who operate it.

2. Apparatus as set forth in claim 1, wherein the enclosure has one end wall portion which is expandable to substantially increase the enclosed work area and which can be placed back in the original enclosure for storage and shipment.

3. Apparatus as set forth in claim 2, wherein the expandable end of the enclosure comprises a floor portion which folds up into the one end of the enclosure for shipping and storage.

4. Apparatus as set forth in claim 3, wherein the expandable floor portion is hinged in the middle whereby the extended floor area is generally twice as long as the enclosure wall portions are high.

5. Apparatus as set forth in claim 4, wherein the middle hinge only rotates 180°.

6. Apparatus as set forth in claim 5 and further comprising a pair of cables connected to the upper portion of the walls of the enclosure and the outer portion of the extended floor portion.

7. Apparatus as set forth in claim 3 and further comprising a fabric member extending from and connected to the roof and side walls of the enclosure and supports connected to the extended floor, the fabric member extending over the supports to form a roof and side walls for the extended work area.

8. Apparatus as set forth in claim 1 wherein the cable is continuous.

9. Apparatus as set forth in claim 8 and further comprising means for storing said tubular extensions with the cable extending therethrough in such a manner that they can be readily connected in series to extend the head assembly deeper into the bore.

10. Apparatus as set forth in claim 1, wherein during operation the trough and shaft are inclined to assist in removing air bubbles from the liquid in the bore.

11. Apparatus as set forth in claim 1, wherein the trough has means for mounting a calibration block disposed in one end thereof.

12. Apparatus as set forth in claim 11, wherein a calibration block having a cylindrical portion generally the same diameter as the bore is disposed in the trough.

13. Apparatus as set forth in claim 11, wherein the end of the trough with the calibration block disposed therein is adjacent one end of the enclosure and has sealing means cooperatively associated therewith for connecting the bore of the shaft to the trough and form a fluid seal therebetween.

14. Apparatus as set forth in claim 13 and further comprising a carriage disposed adjacent the other end of the trough for supporting portions of the tubular extension before they enter the trough and bore.

15. Apparatus as set forth in claim 13, wherein the seal means comprises a spool piece with a gasket on each end thereof.

16. Apparatus as set forth in claim 15, wherein at least the center portion of the spool piece is made of transparent material.

17. Apparatus as set forth in claim 11 and further comprising means for installing and removing calibration blocks from the trough and means for storing the calibration blocks.

18. Apparatus as set forth in claim 17, wherein the means for installing and removing and storing the calibration blocks comprises a beam connected to the enclosure, a trolley which runs on said beam and a hoist connected to said trolley for installing and removing the calibration blocks and a dolly on which the calibration blocks are placed and attached and which are rolled to a storage location and attached to the floor for storage and shipment.

19. Apparatus as set forth in claim 1, wherein the means for producing, receiving and processing said signals is mounted in the enclosure with shock mounts so that it will not be damaged during storage or shipment.

20. Apparatus as set forth in claim 1, wherein the round tubes are made of transparent material so that the head assembly can be observed in the trough.

* * * * *